(12) United States Patent
Colfer

(10) Patent No.: US 7,868,225 B2
(45) Date of Patent: Jan. 11, 2011

(54) ARTICHOKE HYBRID NAMED 'PS-H2015'

(75) Inventor: William J. Colfer, Aptos, CA (US)

(73) Assignees: Plant Sciences, Inc., Watsonville, CA (US); Ocean Mist Farms, Castroville, CA (US)

( * ) Notice: Subject to any disclaimer, the term of this patent is extended or adjusted under 35 U.S.C. 154(b) by 133 days.

(21) Appl. No.: 12/215,466

(22) Filed: Jun. 27, 2008

(65) Prior Publication Data

US 2009/0044299 A1    Feb. 12, 2009

(51) Int. Cl.
*A01H 5/00* (2006.01)
*A01H 5/10* (2006.01)

(52) U.S. Cl. ........................... 800/295; 800/298

(58) Field of Classification Search .............. 800/295, 800/298
See application file for complete search history.

(56) References Cited

U.S. PATENT DOCUMENTS

PP14,578  P2 *   3/2004   Colfer

* cited by examiner

*Primary Examiner*—Medina A. Ibrahim
*Assistant Examiner*—Keith O. Robinson
(74) *Attorney, Agent, or Firm*—Foley & Lardner LLP

(57) ABSTRACT

A new and distinct hybrid of artichoke named 'PS-H2015', characterized by its numerous bud numbers, fleshiness of bracts, fleshiness of hearts, uniformity of head shapes; strong violet blush coloration; and ability to bolt in warm summer conditions (reduced vernalization requirements) allowing spring/summer planting and fall production.

5 Claims, 3 Drawing Sheets
(3 of 3 Drawing Sheet(s) Filed in Color)

ARTICHOKE HYBRID NAMED 'PS-H2015'

FIELD OF INVENTION

The present invention relates to an artichoke hybrid designated 'PS-H2015', as well as, heads produced by this hybrid.

BACKGROUND OF THE INVENTION

The present invention comprises a new and distinct hybrid artichoke variety, botanically known as *Cynara scolymus* L. and herein referred to by the hybrid designation 'PS-H2015'.

*Cynara scolymus* L., commonly known as Globe artichoke, is a thistle-like perennial and is a member of the family *Asteraceae*. Globe artichokes comprise leaves which are pinnately lobed but primarily a spiney and oval capitula composed of an involucre made up of overlapping layers of large bracts and a receptacle which are enlarged and fleshy. Globe artichoke plants may be propagated by division and are essentially grown for the production of the immature flower heads that are vegetable delicacies. Fresh artichokes may be steamed or boiled, after which the fleshy receptacle, inner and outer bracts, and parts of the floral stem may be eaten.

SUMMARY OF THE INVENTION

The new hybrid is a product of a planned breeding program conducted in Chowchilla, Calif. in 2002. The new hybrid is a hybrid produced by crossing 'PS-msC0901' as the female parent (unpatented), and 'RCHB01' as the male parent (unpatented).

An objective of the present invention is to provide seeds to produce artichoke hybrid 'PS-H2015'. Another objective of the present invention is to provide heads produced by the artichoke hybrid 'PS-H2015'.

The new hybrid has not been observed under all possible environmental conditions. The phenotype may vary with variations in environment such as temperature, light intensity and day length, without any change in the genotype of the hybrid.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new Artichoke hybrid 'PS-H2015' showing the colors as true as is reasonably possible with colored reproductions of this type. Colors in the photographs may differ slightly from the color values cited in the detailed botanical description which accurately describes the color of 'PS-H2015'.

Figure 1:

FIG. 1. The first photograph shows an aerial view of many artichoke 'PS-H2015' plants grown in the field.

Figure 2:

FIG. 2. The second photograph shows a side view of many artichoke 'PS-H2015' plants grown in the field.

Figure 3:

FIG. 3. The third photograph shows a close-up side view of the head of an artichoke 'PS-H2015' plant grown in the field.

DETAILED DESCRIPTION

The following observations, measurements and values describe plants of 'PS-H2015' grown in Castroville, Calif., under conditions which closely approximate those generally used in horticultural practice.

'PS-H2015' seeds were deposited at the American Type Culture Collection (ATCC), 10801 University Boulevard, Manassas, Va. 20110-2209 (ATCC Patent Deposit Designation No. PTA-9010). 2500 seeds were deposited with the ATCC on Mar. 6, 2008.

All color references below are measured against The Munsell Book of Color, Munsell Color Macbeth Division of Kollmorgen Instruments Corporation. Colors are approximate as color depends on horticultural practices such as light level and fertilization rate, among others.

Castroville is located in California's central coast. Conditions can vary greatly during the summer months. Air temperature can range between about 20° F. in the winter to above 80° F. during the summer months. Relative humidity is generally moderate with values ranging from the mid 40's to the high 60's. Prevailing winds are westerly and rainfall rarely exceeds 25" inches.

In the following description, holding quality was measured by the physical appearance of the harvested heads. This includes the heads appearance following 3, 7 and 10 day storage periods in a cold storage room held at 34° F. Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosmetic anomalies. Leaf ratio (L/W) was determined by dividing representative leaf sample length measurements by representative leaf sample width measurements. Finally, head response to weather was determined by observing the heads at maturity. These field observations focus on presence or absence of bronzing, necrotic and chlorotic lesions or any abiotic response to environmental conditions. These data are reported as the possible causal event(s) and then describe the detailed head and plant responses.

It should be noted that these data were collected from first year transplants. These data are subject to change depending upon time of planting and environmental conditions. The new and distinct cultivar of artichoke plant named 'PS-H2015' is characterized by:
 1. numerous bud numbers;
 2. fleshiness of bracts;
 3. fleshiness of hearts;
 4. uniformity of head shapes;
 5. strong violet blush coloration; and
 6. ability to bolt in warm summer conditions (reduced vernalization requirements) allowing spring/summer planting and fall production.

---

Parentage:

| | |
|---|---|
| Male parent: | RCHB01 (unpatented) |
| Female parent: | PS-msC0901 (unpatented) |
| Classification: | Botanical: *Cynara scolymus* L. |
| Propagation: | Seed production |

| | |
|---|---|
| Plant: | |
| Height: | About 166.55 cm |
| | Range: 101.60-134.62 cm |
| Width: | About 216.92 cm |
| | Range: 193.04-223.52 cm |
| Growth Habit: | Upright/intermediate |
| Side Shoots: | About 3.20 |
| | Range: 3.0-4.0 |
| Foliage Density: | Open to moderate, variable shoots give plant a open to moderate plant density appearance. Plant development in general is extremely vigorous. |
| Side Shoot Development: | Moderate side shoot development. |
| Capitulum: | |
| Size: | (12) Primary: 36.20-38.10 cm |
| | (18) Secondary: 28.58-30.40 cm |
| | (24) Secondary: 31.12-33.02 |
| | (30) Tertiarty: 28.58-30.48 cm |
| | (36) Tertiarty: 26.04-27.94 cm |
| | (48) Tertiarty: 23.50-25.40 cm |
| Shape: | Oval. Oval shapes are uniform and well distributed. Some heads can have acute apexes. |
| Number: | About 8.25 heads/plant |
| | Range: 6.0-10.0 heads/plant |
| Texture: | Intermediate, smooth. |
| Fragrance: | Mild, lightly aromatic. Aroma is distinct and sweet. |
| Bract Size: | About 9.55 cm (l) × 6.40 cm (w) |
| | Range: 9.20-9.93 cm (l) × 6.27-6.47 cm (w) |
| Bract Shape: | Bracts are predominantly oval shaped with constricted (narrow) basal regions on inner bracts. Some of these basal regions can be rounded at the base. Bract tips can be rounded or slightly split on the terminal end. |
| Bract Texture: | Smooth, slight texture. |
| Bract Number: | About 49.37 bracts |
| | Range: 47-64 bracts |
| Bract Color: | Inner: 2.5 GY 8/8-2.5 GY 8/6-2.5 GY 7/8-2.5 GY 7.6 (Green coloration) |
| | Inner: 2.5 R 3/8-2.5 R 3/6-2.5 R 3/4 (Violet/Anthocyanin Coloration) |
| Bract Basal Thickness: | About 6.52 mm |
| | Range: 4.67-7.67 mm |
| Heart Description: | Concave, full. Heart slightly concave with thick, well developed shoulders. |
| Heart Color: | 5GY 9/1 |
| Papus Length: | About 15.63 mm |
| | Range: 15-17 mm |
| Papus Color: | Variable white coloration. |
| Overall Cold Storage Response: | Good cold storage response. Observations made on day 3, 7 and 10 were good, displaying moderate oxidation (moderate browning on the stem). |
| Head Firmness: | Heads are extremely firm, dense and well-developed. |
| Bract Firmness: | Moderate. Bracts are moderately brittle on the terminal end and extremely brittle and highly turgid on the basal end. |
| Gloss: | Semi-gloss. Heads have slight glossiness in both green and violet portions of the head. |
| Cold Storage (hold quality): | Good. Only moderate "browning" was observed on some terminal ends of stems. |
| Head Exterior (oxidation): | Moderate. Only those areas damaged during harvest showed some oxidation. |
| Juiciness: | Moderate presence. Peduncle and bract exudates are notably visible. |
| Head Response (weather):[1] | None. No adverse plant responses were observed. |
| Foliage: | |
| Length: | About 126.62 cm |
| | Range: 114.50-136.20 cm |
| Width: | About 87.02 cm |
| | Range: 63.20-97.10 cm |
| Leaf Serrations: | About 18.0 mm |
| | Range: 15.0-20.0 mm |
| Leaf Basal Angle: | About 56.90 degrees |
| | Range: 50.00-60.00 degrees |
| Leaf Ratio (L/W): | About 1.47 |
| | Range: 1.33-1.88 |
| Leaf Area: | About 8,132.04 cm$^2$ |
| | Range: 10,293.93-11,942.47 cm$^2$ |
| Color: | 5 GY 3/4-5 GY 4/4-5 GY 5/6-5 GY 5/4 |

| | -continued |
|---|---|
| Texture: | Slightly textured. Immature developing leaves have slightly blistered appearance. Older leaves display increased blistered surface. |
| Venation: | Prominent, white/light green venation. Both mid-vein and surrounding venation are whiter in the basal regions and greener in the terminal regions. |
| Pubescence: | Pubescence on most leaves is indistinct. Immature leaves are only slightly more pubescent. |
| Leaf Basal Thickness: | About 12.10 mm<br>Range: 10.67-12.67 mm |
| Leaf Distance Between Serrations: | About 60.33 mm<br>Range: 47.0-71.0 mm |
| Petiole Length: | About 15.02 cm<br>Range: 12.0-19.5 cm |
| Petiole Width: | About 39.53 mm<br>Range: 30.00-48.00 mm |
| PEST/DISEASE RESISTANCE: | No observations made. |
| PEST/DISEASE SUSCEPTIBILITY: | No observations made. |

[1]Weather means a wide variety of conditions including direct sunlight (warm and sunny) and diffused sunlight (foggy, cool) field conditions.
[2]These numbers reflect the number of artichoke heads required to fill a standard artichoke carton. For example, the small 36 size requires 36 artichokes of that size to fill the carton.

Artichoke hybrid 'PS-H2015' produces plants with a moderate height, ranging from 101-134 cm. In comparison to artichoke hybrid 'Green Globe', 'PS-H2015' has a very different green violet (slightly-glossy) exterior coloration, but a greater number of heads per plant. Head numbers are about 6-10 per 'PS-H2015' plant. Head shape is predominately oval. The slightly glossy heads are produced in sizes ranging from size (12) primary, size (18), (24) secondary and sizes (30, 36 and 48) tertiary.[2] Anthocyanin coloration is present on the innermost interior bracts and found on the outer, exterior bracts. These colors on Munsell Leaf Color Chart range from 2.5 R ⅜-2.5 R ⅝-2.5 R ¾. Its presence is characterized as distinct and is most prominent in the basal portions of the head. The head spinosity is slightly more prominent on bract apexes that are acute. Although they are reduced in length they generally are always present. The average spine length ranges between 1.0-3.0 mm. The plants upright growth habit is intermediate, but is very vigorous. The canopies coloration is a deeper green color with some colors ranging towards darker green/green/grey hues. These colors on Munsell Leaf Color Chart range from 5 GY ¾-5 GY ⁴⁄₄-5 GY ⅝-5 GY ⅝. Leaf spinosity is light to moderate, categorized as few. Floral stalk development during anthesis produces a purple flower. Flower color changes as the flower matures. The phenotypic characteristics of this cultivar may vary slightly, depending upon variation in the environmental factors, including weather (temperature, humidity and light intensity), day length, soil type, farming practices, location and time of year.

What is claimed is:

1. Seed of artichoke variety PS-H2015, a sample of seed having been deposited under American Type Culture Collection Deposit Accession No. PTA-9010.

2. An artichoke plant produced by growing the seed of claim 1.

3. Pollen of the plant of claim 2.

4. A plant part of claim 2.

5. Head of the plant of claim 2.

* * * * *